United States Patent [19]

Firca et al.

[11] 4,276,050
[45] Jun. 30, 1981

[54] METHOD FOR SYSTEMIC ENDOTOXIN DETECTION

[75] Inventors: Joseph R. Firca, Vernon Hills, Ill.; Jon A. Rudbach, Missoula, Mont.

[73] Assignee: Abbott Laboratories, North Chicago, Ill.

[21] Appl. No.: 110,872

[22] Filed: Jan. 10, 1980

[51] Int. Cl.$^3$ .................. G01N 31/08; G01N 33/92
[52] U.S. Cl. .................. 23/230 B; 210/635; 435/4
[58] Field of Search .................. 23/230 B; 435/4; 210/31 C, 635

[56] References Cited

U.S. PATENT DOCUMENTS

| | | | |
|---|---|---|---|
| 3,527,712 | 9/1970 | Renn | 210/635 X |
| 3,944,391 | 3/1976 | Harris | 23/230 B |
| 4,020,268 | 4/1977 | Nishikawa | 536/1 |
| 4,038,029 | 7/1977 | Teller | 23/230 B |
| 4,096,091 | 6/1978 | Hopkins | 435/7 |
| 4,104,030 | 8/1978 | Hopkins | 23/230 B |
| 4,107,077 | 8/1978 | Sullivan | 23/230 B |
| 4,125,492 | 11/1978 | Cuatrecasas | 210/635 X |
| 4,138,474 | 2/1979 | Updike | 210/635 X |
| 4,143,201 | 3/1979 | Miyashiro | 210/635 X |
| 4,162,355 | 7/1979 | Tsibris | 210/31 C |
| 4,188,264 | 2/1980 | Iwanaga | 435/19 X |

OTHER PUBLICATIONS

Chemical Abstracts, 87: p. 3191h (1977).
Munford, et al., Infection and Immunity, vol. 26, No. 1, Oct. 1979, pp. 42-48; Radioimmunoassay for Gram-Negative Bacterial Lipopolysaccharide O Antigens: Influence of Antigen Solubility.
Rudbach, et al., Annals of the New York Academy of Science (Reprint), vol. 133, Article 2, pp. 629-643, Jun. 30, 1966; Physical Aspects of Reversible Inactivation of Endotoxin.
Nolan, et al., Proceedings of the Society for Experimental Biology and Medicine, 149, pp. 766-770, (1975); Endotoxin Binding by Charged and Uncharged Resins.
Saunders, et al., The School of Pharmacy, University of London and Elga Products Limited, Lane End, pp. 410-415, 1970; Preparation of Biologically Pure Water by Ion Exchange.
Rubio, et al., J. Chromatogr., 57, (1971), pp. 148-150; Purification of *Pseudomonas Aeruginosa* Endotoxin by Gel Filtration on Sepharose 4B.
Romanowska, Analytical Biochemistry, 33, pp. 383-389, (1970); Sepharose Gel Filtration Method of Purification of Lipopolysaccharides.
Romanowska, et al., Febs Letters, vol. 66, No. 1, Jul. 1976, pp. 82-85; Lipopolysaccharide Immunoadsorbents and Their Application to Affinity Chormatography of O-Antibodies and Specific Phages.
Bader, et al., Z. Naturforsch (C), vol. 28, No. 7, pp. 422-430, Jul.-Aug., 1973; Action of Polymyxin B on Bacterial Membranes, I.
Gyulbadamova, et al., Probl. Gematol. Pereliv. Krovi, vol. 11, No. 7, pp. 19-23, Jul. 1966; The Mechanism of Detoxifying Effective of PVP in Burns and in Food Poisoning (In Russian-English/Russian Summary).
Rudbach, et al., Society for Experimental Biology and Medicine (Reprint), vol. 119, pp. 115-118, 1965, Reactivation of Papain-Treated Endotoxin (30112).
Rudbach, et al., Nature, (Reprint) vol. 202, No. 4934, pp. 811-812, May 23 1964, Restoration of Endotoxin Activity Following Alteration by Plasma.
Limulus Amebocyte Lysate (Pyrotell) for the Detection and Quantitation of Endotoxins, Associates of Cape Cod, Inc., Woods Hole, MA.
The Limulus Amebocyte Lysate (LAL) Test for Endotoxin in Human Plasma, Gaffin, et al.

*Primary Examiner*—Sidney Marantz
*Attorney, Agent, or Firm*—John J. McDonnell

[57] ABSTRACT

A method for detecting endotoxins in body fluids comprising: unmasking endotoxins in the body fluids; separating the unmasked endotoxins from the body fluids by affinity chromatography; and detecting the endotoxins. This method is particularly useful for early detection of life threatening systemic Gram-negative infections.

4 Claims, No Drawings

METHOD FOR SYSTEMIC ENDOTOXIN DETECTION

BACKGROUND OF THE INVENTION

Systemic bacterial infection caused by Gram-negative bacteria represents a serious health problem resulting in over 100,000 deaths per year in the United States. At least 1% of all patients admitted to hospitals either have or acquire, during their stay, Gram-negative septicemia. Once a patient enters into septicemic shock the death rate is about 50%. It is therefore critical that these infections be detected at the preshock stage.

Classically bacterial infections are detected by culturing a sample of a body fluid for 2-14 days, measuring bacterial growth, and identifying the organisms.

It is known that bacteria release endotoxins during lysis. Endotoxins are lipopolysaccharides associated with various amounts of protein and lipid, the biological activity residing primarily with the lipopolysaccharides.

When admitted to the bloodstream of animals endotoxins initiate a complex chain of biochemical reactions which result in an elevation in body temperature (fever) and as a result these substances have been referred to as pyrogens.

In fact, a commonly used test for detecting endotoxins in intravenous solutions and other parenterally administered pharmaceutical preparations is the so-called rabbit fever test. In this test, rabbits are injected with a portion of the parenteral preparation to be tested and their temperature is monitored, an elevated temperature being a positive test for the presence of endotoxins (pyrogens).

Endotoxins can also be detected in picogram/ml quantities by the Limulus Amoebocyte Lysate method, described in New England Journal of Medicine, Vol. 289, No. 18, 931-934 (1973) and U.S. Pat. No. 4,107,007, Aug. 15, 1978. Limulus amoebocyte lysate is an aqueous extract of blood cells (amoebocytes) from the horseshoe crab, Limulus polyphemus. The endotoxins activate an enzyme in the Limulus amoebocyte lysate which then reacts with low molecular weight clottable proteins to form a gel. Typically, 0.1 ml solution of a freeze-dried Limulus lysate preparation sold commercially under the trademark Pyrotell ® by Associates of Cape Cod, Inc. is mixed with 0.1 ml of a test sample, then allowed to incubate undisturbed for one hour at 37° C. A positive test is indicated by the formation of a gel which does not collapse upon 180 degree inversion of the test tube.

Despite the existence of methods for detecting endotoxins at extremely low concentrations and the critical need to detect endotoxins in body fluids, there presently are no reliable methods for detecting endotoxin levels in body fluids such as blood, plasma, and serum. There are a number of difficulties residing in measuring endotoxins in body fluid.

The biological activities of endotoxins in body fluids are to varying degrees masked by the association of the endotoxin with protein and lipid.

For example, Journal of Bacteriology, 92, No. 4, 892-892, (1966) describes alteration and restoration of endotoxin activity after complexing with plasma protein. Also see Annals of the New York Academy of Sciences, Vol. 133, 629-643 (1966) for a discussion of the physical aspects of reversible inactivation of endotoxins.

It is therefore recognized that chemical dissociation of endotoxin complexes in biological fluids will unmask the endotoxin so that it will exhibit its full biological activity, e.g. pyrogenicity.

Body fluids are also known to contain inhibitors to the Limulus amoebocyte lysate test, Riegle and Cooperstock, Laboratory Medicine, 8, 28, (1977). There have been a number of attempts to inactivate Limulus amoebocyte lysate inhibitors in serum and plasma, Journal of Laboratory and Clinical Medicine, 75, 903 (1970); Proceedings of the Society of Experimental Biology and Medicine, 137, (1971); and Laboratory Medicine, 8, 28, (1977).

The above-mentioned difficulties are compounded by the extremely low concentrations of endotoxin in body fluids and the need to detect the endotoxins in the preshock stage of the infection. The invention overcomes the problems associated with detection and quantification of endotoxins in body fluids.

SUMMARY OF THE INVENTION

This invention encompasses a method for detecting endotoxins in body fluid which comprises unmasking endotoxins in the body fluid, separating the unmasked endotoxins from the body fluid by affinity chromatography, and detecting the endotoxin. The endotoxin may be detected while on the column or upon elution from the column. This invention provides for umasking endotoxins in body fluids, concentrating those endotoxins on an affinity chromatography column and at the same time separating substances in the body fluid which may interfere with endotoxin detection. Although particularly applicable to endotoxin detection in body fluids, it is understood that the method is equally applicable to other solutions containing endotoxin concentrations and/or where separation of inhibitors are desired.

DETAILED DESCRIPTION OF THE INVENTION

Endotoxins in body fluids are unmasked by treatment with salt, detergent, or organic chemical solutions such as: 2% Tween-80 (Polyethoxy Sorbitan Monooleate), 2% dextransulfate, 3% sodium chloride, or 2% ammonium thiocyanate. Solutions of benzamidine or its biologically compatible acid addition salts of about 0.002 molar are preferred reagents for unmasking endotoxins in body fluids. Those skilled in the biochemical art will recognize a wide variety of equivalent salts, detergents, and organic chemicals which will dissociate endotoxin (Lipopolysaccharides) in body fluids so that they exhibit their biological activity. In a preferred unmasking procedure, 1 ml of 0.002 molar benzamidine is added to an equal volume of body fluid and followed by gentle mixing.

Matrices suitable for both concentrating and separating endotoxins are described in an invention entitled Adsorbant For Endotoxins and Method of Removal of Endotoxins, inventors Ronald L. Gendrich and William H. Holleman, filed on the same date as this application and assigned to the same assignee as this application Ser. No. 110,871, filed Jan. 10, 1980. A matrix material capable of binding endotoxins, is described therein and has the formula:

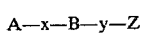

wherein A is an insoluble polymer; x is a first linking group comprising isourea, an ester, an ether, or an amine; B is a spacer group comprising a straight, branched or cyclic alkyl of from 1–12 carbon atoms, hydroxyl, loweralkylamine, loweralkylether, or loweralkylthioether; y is a second linking group comprising a methylene, an ether, thioether or an amide; and Z is an aryl nucleus group, either unsubstituted or substituted with one or more amidino, guanidino, amino, carboxamido, hydroxyl, halo, nitro, alkyl or alkoxy.

An example of a suitable matrix material is agaroseisoureidohexanoyl-meta-benzamidineamide,

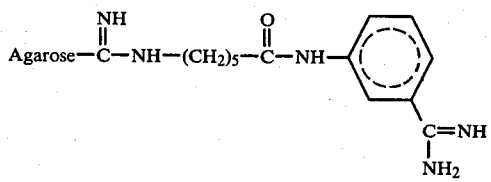

Suitable support substances include cellulose, cellulose acetate or nitrate, agarose, polymethacrylate or polystyrene.

Some examples of matrix materials differing in composition of the spacer (B) are as follows:

—C$_4$H$_8$—

—C$_5$H$_{10}$—

—C$_6$H$_{12}$—

—C$_7$H$_{14}$—

—C$_{11}$H$_{22}$—

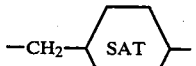

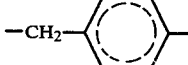

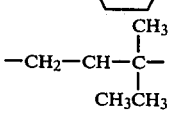

—(CH$_2$)$_2$—NH—(CH$_2$)$_2$—

—(CH$_2$)$_3$—S—(CH$_2$)$_3$—

Examples of matrix materials differing in composition of the second linking group are as follows:
Support-Link 1-Spacer-Link 2-Aryl Nucleus

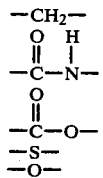

The following are examples of matrix materials differing in composition of the aryl molecule:
Support-Link 1-Spacer-Link 2-Aryl Molecule

phenyl

benzyl

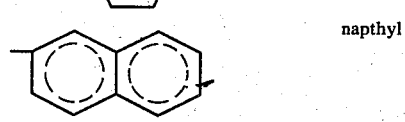
napthyl

Examples of matrix materials differing in composition of the substituted Aryl group:
Support-Link 1-Spacer-Link 2-Substituted Aryl Group

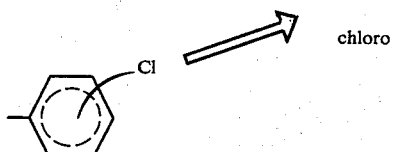
chloro

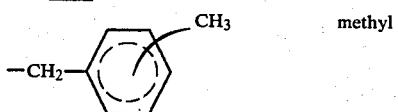
methyl

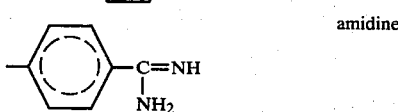
amidine

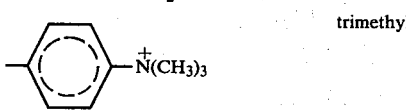
trimethylamino

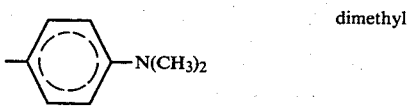
dimethylamino

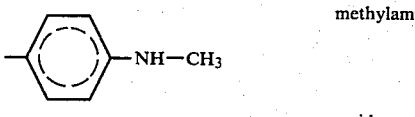
methylamino

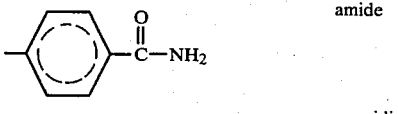
amide

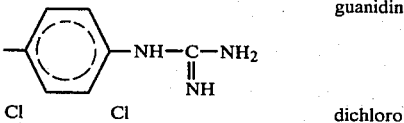
guanidinium

dichloro

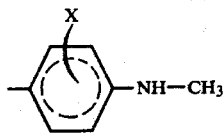

X = Halogen or loweralkoxy

The term "loweralkyl", as used herein, refers to straight or branched chain alkyl radicals containing from 1 to 6 carbon atoms including but not limited to methyl, ethyl, n-propyl, iso-propyl, n-butyl, sec-butyl, 2-methyhexyl, n-pentyl, 1-methylbutyl, 2,2-dimethylbutyl, 2-methylpentyl, 2,2-dimethylpropyl, n-hexyl and the like.

The term "alkyl" refers to straight, branched or cyclic alkyl radicals containing from 1 to 12 carbon atoms.

The term "aryl" includes phenyl, naphthyl or benzyl.

The term "substituted aryl" includes aryl groups substituted by secondary, tertiary or quaternary ammonium, amidinium or guanidinium or by one or more halo or loweralkoxy.

A suitable material may be prepared as follows:

45 gm of 6-aminohexanoic acid, suspended in 25 ml water, is mixed with 100 ml of packed Sepharose ™ (agarose gel beads). The pH of the mixture is adjusted to 10.5 by the addition of a saturated solution of NaOH in water. The temperature of the suspension is adjusted to 15° C. by the addition of chunks of ice. Eighty grams of solid CNBr is added to the suspension over a 15 minute period.

Rapid stirring is maintained. The pH is maintained at 10.5±0.5 by the addition of saturated NaOH. The temperature is maintained at 17.5°±2.5° C. by the addition of ice. After the reaction mixture has stopped consuming base, excess reagents are removed by filtering the solid, derivatized agarose on a coarse sintered glass filter, then washing it in place by the addition of several bed volumes of 1 M NaCl, then several bed volumes of 1 N acetic acid, finally with at least 5 bed volumes of water.

The suspension of Agarose-6-aminohexanoic acid isourea is then transferred to a beaker, adding about 250 ml of water. Fifty grams of 1-ethyl-3(3 dimethylaminopropyl) carbodiimide (EDC) are added as solids. The EDC dissolves rapidly and reacts with the agarose derivative to form an active ester. The suspension is stirred 30 minutes to permit the active ester formation to occur. Ten grams of meta-amino benzamidine hydrochloride in water solution, neutralized to pH 4, is then added. The pH of the reaction is adjusted to 4.5±0.5 and maintained at that value for 24 hours, preferably at 4° C. A sample is then removed.

The degree of substitution of the sample is determined by the indirect method of Hoare and Koshland, JBC, 242, 244 (1967).

The degree of substitution was 12.75±0.25 ueq. 6 aminohexanoic acid (6AHA)/ml of beads. The degree of incorporation of benaamidine was 11.6 ueq/ml gel or 91% of the 6AHA.

An additional 50 grams of EDC are then added to the suspension. 6 molar ethanolamine HCl, pH 6±1, is then added to a final ethanolamine concentration of 0.4 M. The pH is maintained at 5.0±0.5 for an additional 24 hours. The product, SAB, is now washed as above with 3 bed volumes of 1 M NaCl solution, with 3 bed volumes of N acetic acid and with 3 bed volumes of water. If extended storage is required, the addition of 0.1% trichlorobutanol in the final wash is useful as a preservative.

Polymeric matrices having endotoxin (lipopolysaccharide) binding substance bound thereto are suitable for practicing this invention.

Matrices of the type described in Belgium Pat. No. 848,175 and U.S. Pat. No. 4,020,248 and ion exchange resins Proc. Soc. Biol. Med. 149, 766 (1975) are also useful for separating endotoxins. Those skilled in the chromatography arts will recognize a wide variety of molecular modifications in matrix structure which are useable.

The above-described SAB matrix is preferred by virtue of its extremely high affinity for endotoxins. The endotoxin bound to the matrix can be detected while on the affinity column, for example, by use of a labeled antibody to the endotoxin as described in Infection and Immunity, 26, Vol. 1 (1979) p 42–48.

Generally, the column is washed to remove interfering substances. A variety of organic and inorganic acid, detergent, and salt solutions are effective in washing the column. The wash solution should have sufficient ionic strength to retain protein in solution so the column is not blocked. Normal saline or dilute acetic acid solution are preferred washes. A variety of other washes are suitable, for example:

1% Tween 80 or Tween 20
0.01 M Hydrochloric acid
1% Benzamidine hydrochloride
1% Ammonium thiocyanate
1% Dextran sulfate
2 to 4 M Urea
5% Sodium bicarbonate
1 Molar metal salts such as:
   Magnesium chloride
   Calcium chloride
   Chromic chloride
   Ferric chloride
   Cupric sulfate
1 M Triethylamine hydrochloride
Fatty acids such as:
Palmitic
Myristic
Lauric
Oleic have all been found to be useful washes.

The endotoxins are eluted from the column with strong detergent or salt solutions such as 2% sodium dodecylsulfate, 3% sodium deoxycholate or 2 molar magnesium chloride.

The endotoxins in the eluent are precipitated by treatment with cold alcohol, preferably ethanol. The endotoxins are collected after centrifugation and detected by Limulus amoebocyte lysate or rabbit fever test.

Those skilled in the chromatography art will recognize a variety of matrices, washes, eluents for separating lipopolysaccharide (endotoxin) material.

EXAMPLE 1

To 1 ml of heparinized plasma is added 1 ml of 0.002 molar benzamidine and the liquids are gently mixed. This mixture is added to 2.0 cubic centimeter bed volume of SAB on a column. The mixture is allowed to flow freely through the resin. Care must be taken to prevent extraneous endotoxin from entering at this or any other step in the assay. All reagents and containers are sterile and pyrogen free.

Once the entire volume of the reaction mixture has passed over the column, the column is washed with 2 ml of normal saline (0.15 molar or 0.9%) to remove weakly bound contaminants from the plasma. The column is then washed with 8 ml of 0.005 N acetic acid to remove the tightly bound contaminants from the column.

The endotoxin is eluted from the column with 5.0 ml of 2% sodium dodecylsulfate. The eluate is treated with 25 ml of ice cold ethanol and incubated for 15–30 minutes in an ice bath. The mixture is centrifuged and supernantant discarded. The precipitate is reconstituted in 1 ml of pyrogen free distilled water.

The endotoxin is detected by the Limulus amoebocyte lysate test. 0.1 ml of Pyrotell ® a Limulus amoebocyte lysate preparation sold under the tradename Pyrotell ® by Associates of Cape Cod, Inc., Woods Hole, Mass., is mixed with 0.1 ml of test sample, then allowed to incubate undisturbed for one hour at 37° C. A positive test is indicated by the formation of a gel which does not collapse upon 180 degree inversion of the test tube. To quantitate the amount of endotoxin in body fluid, serial dilution of test samples are tested with Limulus amoebocyte lysate preparation to determine the lowest dilution which will give the above-described positive result.

What is claimed is:
1. A method for detecting endotoxins in body fluids comprising:
    (a) unmasking endotoxins in the body fluid;
    (b) separating the unmasked endotoxins from the body fluid by affinity chromatography; and
    (c) detecting the endotoxins.
2. A method, according to claim 1, wherein the endotoxin is detected while bound to an affinity chromatography matrix.
3. A method, according to claim 1, wherein the endotoxin is detected after elution from an affinity chromatography matrix.
4. A method, according to claim 3, wherein the endotoxin is detected by the Limulus amoebocyte lysate test for endotoxins.

* * * * *